United States Patent
Chopra et al.

(10) Patent No.: US 10,499,993 B2
(45) Date of Patent: Dec. 10, 2019

(54) SYSTEMS AND METHODS FOR NON-RIGID DEFORMATION OF TISSUE FOR VIRTUAL NAVIGATION OF INTERVENTIONAL TOOLS

(71) Applicant: INTUITIVE SURGICAL OPERATIONS, INC., Sunnyvale, CA (US)

(72) Inventors: Prashant Chopra, Foster City, CA (US); Vincent Duindam, San Francisco, CA (US); Lei Xu, Mountain View, CA (US); Tao Zhao, Sunnyvale, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

(21) Appl. No.: 16/405,438

(22) Filed: May 7, 2019

(65) Prior Publication Data
US 2019/0254752 A1 Aug. 22, 2019

Related U.S. Application Data

(63) Continuation of application No. 15/116,115, filed as application No. PCT/US2015/014226 on Feb. 3, 2015, now Pat. No. 10,314,656.
(Continued)

(51) Int. Cl.
*A61B 34/10* (2016.01)
*A61B 34/30* (2016.01)
(Continued)

(52) U.S. Cl.
CPC .............. *A61B 34/10* (2016.02); *A61B 34/20* (2016.02); *A61B 34/30* (2016.02); *G06T 19/20* (2013.01);
(Continued)

(58) Field of Classification Search
CPC ......... A61B 34/10; A61B 34/20; A61B 34/30; A61B 2034/105; A61B 2034/107;
(Continued)

(56) References Cited

U.S. PATENT DOCUMENTS

| 6,380,732 B1 | 4/2002 | Gilboa et al. |
| 6,389,187 B1 | 5/2002 | Greenaway et al. |
(Continued)

FOREIGN PATENT DOCUMENTS

| CN | 101961245 A | 2/2011 |
| CN | 102970926 A | 3/2013 |
(Continued)

OTHER PUBLICATIONS

International Preliminary Report on Patentability for Application No. PCT/US15/14226, dated Aug. 18, 2016, 9 pages.
(Continued)

*Primary Examiner* — Edward Park
(74) *Attorney, Agent, or Firm* — Haynes & Boone, LLP (57) ABSTRACT

A processing system comprises a processor and a memory having computer readable instructions stored thereon. The computer readable instructions, when executed by the processor, cause the system to receive a reference three-dimensional volumetric representation of a branched anatomical formation in a reference state and obtain a reference tree of nodes and linkages based on the reference three-dimensional volumetric representation. The computer readable instructions also cause the system to obtain a reference three-dimensional geometric model based on the reference tree and detect deformation of the branched anatomical formation due to anatomical motion based on measurements from a shape sensor. The computer readable instructions also cause the system to obtain a deformed tree of nodes and linkages based on the detected deformation, create a three-
(Continued)

dimensional deformation field that represent the detected deformation of branched anatomical, and apply the three-dimensional deformation field to the reference three dimensional geometric model.

20 Claims, 9 Drawing Sheets

Related U.S. Application Data (60) Provisional application No. 61/935,547, filed on Feb. 4, 2014.

(51) Int. Cl.
*A61B 34/20* (2016.01)
*G06T 19/20* (2011.01)

(52) U.S. Cl.
CPC ... *A61B 2034/105* (2016.02); *A61B 2034/107* (2016.02); *A61B 2034/2051* (2016.02); *A61B 2034/2061* (2016.02); *A61B 2034/301* (2016.02); *G06T 2210/41* (2013.01); *G06T 2219/2021* (2013.01)

(58) Field of Classification Search
CPC .... A61B 2034/2051; A61B 2034/2061; A61B 2034/301; G06T 19/20; G06T 2219/2021
See application file for complete search history.

(56) References Cited

U.S. PATENT DOCUMENTS

| | | | |
|---|---|---|---|
| 7,772,541 | B2 | 8/2010 | Froggatt et al. |
| 7,781,724 | B2 | 8/2010 | Childers et al. |
| 7,930,065 | B2 | 4/2011 | Larkin et al. |
| 8,900,131 | B2 | 12/2014 | Chopra et al. |
| 10,314,656 | B2 | 6/2019 | Chopra et al. |
| 2005/0182295 | A1 | 8/2005 | Soper et al. |
| 2006/0013523 | A1 | 1/2006 | Childers et al. |
| 2006/0149134 | A1 | 7/2006 | Soper et al. |
| 2007/0167738 | A1 | 7/2007 | Timinger et al. |
| 2007/0231779 | A1 | 10/2007 | Santhanam et al. |
| 2008/0118135 | A1 | 5/2008 | Averbuch et al. |
| 2008/0171934 | A1 | 7/2008 | Greenan et al. |
| 2008/0193904 | A1* | 8/2008 | Santhanam ............ G09B 23/28 434/272 |
| 2009/0227861 | A1 | 9/2009 | Ganatra et al. |
| 2011/0093243 | A1 | 4/2011 | Tawhai et al. |
| 2013/0303893 | A1* | 11/2013 | Duindam ............... A61B 5/066 600/424 |
| 2014/0267252 | A1 | 9/2014 | Hutchinson et al. |

FOREIGN PATENT DOCUMENTS

| | | |
|---|---|---|
| CN | 103079478 A | 5/2013 |
| JP | H09131344 A | 5/1997 |
| JP | 2011092263 A | 5/2011 |
| WO | WO-2008041165 A2 | 4/2008 |
| WO | WO-2008076910 A1 | 6/2008 |
| WO | WO-2009147683 A1 | 12/2009 |
| WO | WO-2010111090 A1 | 9/2010 |

OTHER PUBLICATIONS

International Search Report and Written Opinion for Application No. PCT/US15/14226, dated May 20, 2015, 12 pages.

Mariampillai A., et al., "Doppler Optical Cardiogram Gated 2D Color Flow Imaging at 1000 Fps and 4D in Vivo Visualization of Embryonic Heart at 45 fps on a Swept Source OCT System," Optics Express, Feb. 2007, vol. 15 (4), pp. 1627-1638.

Extended European Search Report for Application No. 15745879.5, dated Oct. 11, 2017, 7 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

$w_0 = P - P_0$ and $\theta_0 \in [-180°, 180]$
$w_0 \cdot v \leq 0$
$\quad \Leftrightarrow |\theta_0| \geq 90°$ is obtuse
$\quad \Leftrightarrow d(P,S) = d(P,P_0)$ $w_1 = P - P_1$ and $\theta_1 \in [-180°, 180]$
$w_1 \cdot v \geq 0 \Leftrightarrow w_0 \cdot v \geq v \cdot v$
$\quad \Leftrightarrow |\theta_1| \leq 90°$ is acute
$\quad \Leftrightarrow d(P,S) = d(P,P_1)$

Fig. 16

SYSTEMS AND METHODS FOR NON-RIGID DEFORMATION OF TISSUE FOR VIRTUAL NAVIGATION OF INTERVENTIONAL TOOLS

CROSS-REFERENCE TO RELATED APPLICATIONS

The present application is a continuation of U.S. patent application Ser. No. 15/116,115, filed Aug. 2, 2016, now U.S. Pat. No. 10,314,656, which is the U.S. National Phase of International Application No. PCT/US2015/014226, filed Feb. 3, 2015, which designated the U.S. and claims priority to U.S. Provisional Patent Application No. 61/935,547, filed on Feb. 4, 2014 and entitled "Systems and Methods for Non-Rigid Deformation of Tissue for Virtual Navigation of Interventional Tools," all of which are hereby incorporated herein by reference in their entirety.

FIELD

The present disclosure is directed to systems and methods for navigating a patient anatomy to conduct a minimally invasive procedure, and more particularly to systems and methods for dynamically deforming an anatomical passageway model for display.

BACKGROUND

Minimally invasive medical techniques are intended to reduce the amount of tissue that is damaged during interventional procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. To reach the target tissue location, a minimally invasive interventional instrument may navigate natural or surgically created passageways in anatomical systems such as the lungs, the colon, the intestines, the kidneys, the heart, the circulatory system, or the like. Teleoperated interventional systems may be used to insert and position the interventional instrument within the patient anatomy. During navigation of the interventional instrument, the anatomical passageways may deform due to, for example, anatomical motion (e.g. cardiac motion, respiration motion) or a force applied by the interventional instrument. Systems and methods are needed to dynamically deform anatomical passageway models for display to a user while navigating the actual patient anatomical passageways with the interventional instrument.

SUMMARY

The embodiments of the invention are summarized by the claims that follow the description.

In one embodiment, method of modeling anatomic deformation comprises receiving a reference three dimensional model of a branched anatomical formation in a reference state. The method further comprises applying a three dimensional deformation field to the reference three dimensional model to create a deformed three dimensional model of a deformed state of the branched anatomical formation and dynamically displaying an image of the deformed three dimensional model of the deformed state of the branched anatomical formation.

In another embodiment, a processing system comprises a processor and a memory having computer readable instructions stored thereon. The computer readable instructions, when executed by the processor, cause the system to receive a reference three dimensional model of a branched anatomical formation in a reference state. The instructions when executed by the processor also cause the system to apply a three dimensional deformation field to the reference three dimensional model to create a deformed three dimensional model of a deformed state of the branched anatomical formation. The instructions when executed by the processor also cause the system to dynamically display an image of the deformed three dimensional model of the deformed state of the branched anatomical formation.

Additional aspects, features, and advantages of the present disclosure will become apparent from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object.

Figure 1:
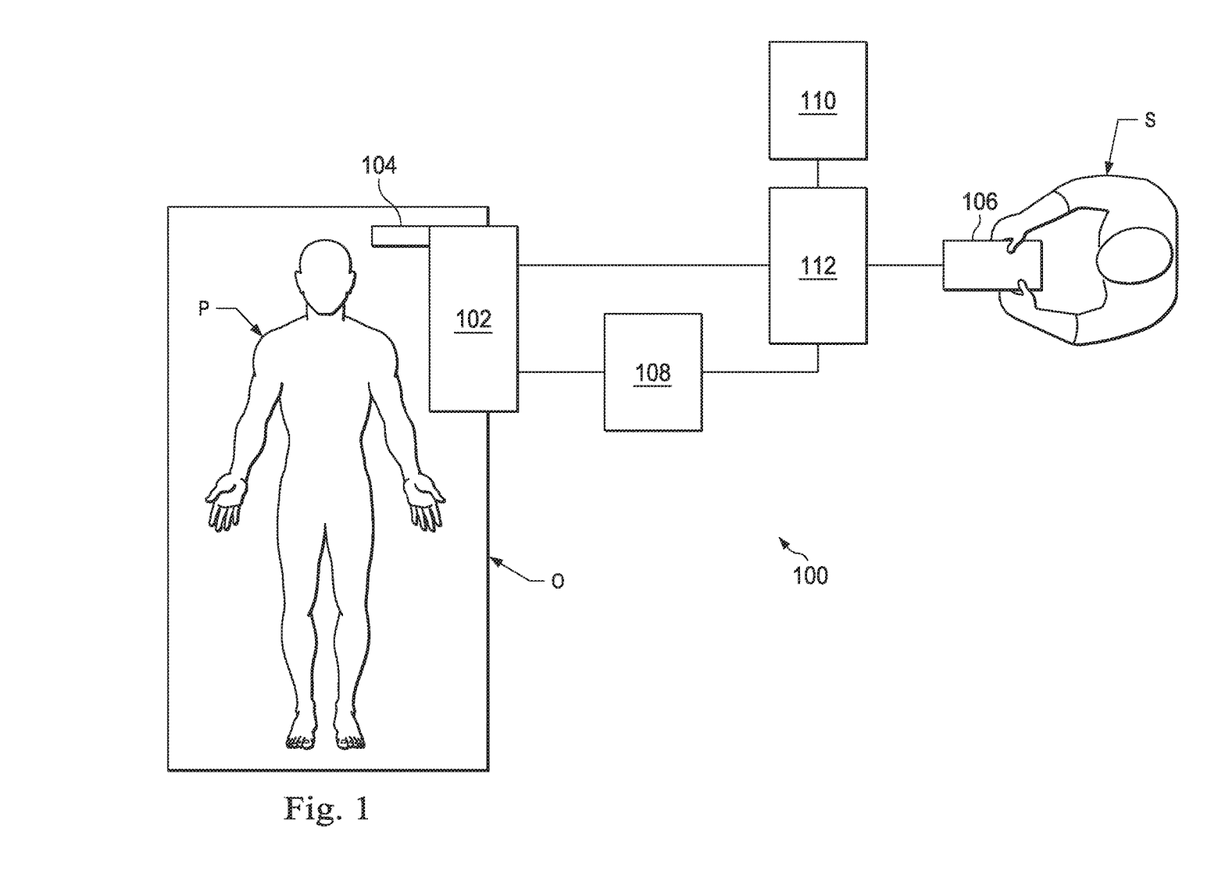
FIG. 1 is a telerobotic interventional system, in accordance with an embodiment of the present disclosure.

Referring to FIG. 1 of the drawings, a telerobotic interventional system for use in, for example, surgical, diagnostic, therapeutic, or biopsy procedures, is generally indicated by the reference numeral 100. As will be described, the telerobotic interventional systems of this disclosure are generally under the teleoperational control of a surgeon. However, for some procedures or sub-procedures, the telterobotic interventional system may be under the partial or full control of a computer programmed to perform the procedure or sub-procedure. As shown in FIG. 1, the telerobotic interventional system 100 generally includes a robotic assembly 102 mounted to or near an operating table O on which a patient P is positioned. An interventional instrument system 104 is operably coupled to the robotic assembly 102. An operator input system 106 allows a surgeon or other type of clinician S to view the surgical site and to control the operation of the interventional instrument system 104.

The operator input system 106 may be located at a surgeon's console which is usually located in the same room as operating table O. However, it should be understood that the surgeon S can be located in a different room or a completely different building from the patient P. Operator input system 106 generally includes one or more control device(s) for controlling the interventional instrument system 104. The control device(s) may include any number of a variety of input devices, such as hand grips, joysticks, trackballs, data gloves, trigger-guns, hand-operated controllers, voice recognition devices, touch screens, body motion or presence sensors, or the like. In some embodiments, the control device(s) will be provided with the same degrees of freedom as the interventional instruments of the robotic assembly to provide the surgeon with telepresence, or the perception that the control device(s) are integral with the instruments so that the surgeon has a strong sense of directly controlling instruments. In other embodiments, the control device(s) may have more or fewer degrees of freedom than the associated interventional instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, or the like).

The robotic assembly 102 supports the interventional instrument system 104 and may comprise a kinematic structure of one or more non-servo controlled links (e.g., one or more links that may be manually positioned and locked in place, generally referred to as a set-up structure) and a robotic manipulator. The robotic assembly 102 includes plurality of actuators (e.g., motors) that drive inputs on the interventional instrument 104. These motors actively move in response to commands from the control system (e.g., control system 112). The motors include drive systems which when coupled to the interventional instrument 104 may advance the interventional instrument into a naturally or surgically created anatomical orifice and/or may move the distal end of the interventional instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulable end effector of the instrument for grasping tissue in the jaws of a biopsy device or the like.

The robotic interventional system 100 also includes a sensor system 108 with one or more sub-systems for receiving information about the instruments of the robotic assembly. Such sub-systems may include a position sensor system (e.g., an electromagnetic (EM) sensor system); a shape sensor system for determining the position, orientation, speed, pose, and/or shape of the catheter tip and/or of one or more segments along a flexible body of instrument 104; and/or a visualization system for capturing images from the distal end of the catheter system.

The robotic interventional system 100 also includes a display system 110 for displaying an image of the surgical site and interventional instruments 104 generated by sub-systems of the sensor system 108. The display 110 and the operator input system 106 may be oriented so the operator can control the interventional instrument system 104 and the operator input system 106 as if viewing the workspace in substantially true presence. True presence means that the displayed tissue image appears to an operator as if the operator was physically present at the image location and directly viewing the tissue from the perspective of the image.

Alternatively or additionally, display system 110 may present images of the surgical site recorded and/or modeled preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. The presented preoperative or intra-operative images may include two-dimensional, three-dimensional, or four-dimensional (including e.g., time based or velocity based information) images and models.

In some embodiments, the display system 110 may display a virtual visualization image in which the actual location of the interventional instrument is registered (e.g., dynamically referenced) with preoperative or concurrent images to present the surgeon with a virtual image of the internal surgical site at the location of the tip of the surgical instrument.

In other embodiments, the display system 110 may display a virtual visualization image in which the actual location of the interventional instrument is registered with prior images (including preoperatively recorded images) or concurrent images to present the surgeon with a virtual image of an interventional instrument at the surgical site. An image of a portion of the interventional instrument 104 may be superimposed on the virtual image to assist the surgeon controlling the interventional instrument.

The robotic interventional system 100 also includes a control system 112. The control system 112 includes at least one memory and at least one processor (not shown), and typically a plurality of processors, for effecting control between the interventional instrument system 104, the operator input system 106, the sensor system 108, and the display system 110. The control system 112 also includes programmed instructions (e.g., a computer-readable medium storing the instructions) to implement some or all of the methods described herein. While control system 112 is shown as a single block in the simplified schematic of FIG. 1, the system may comprise a number of data processing circuits with a portion of the processing optionally being performed on or adjacent the robotic assembly 102, a portion being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the robotic systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers to provide force and torque feedback from the interventional instrument system 104 to one or more corresponding servomotors for the operator input system 106. The servo controller(s) may also transmit signals instructing robotic assembly 102 to move the interventional instruments 104 which extend into an internal surgical site within the patient body via openings in the body. Any suitable conventional or specialized servo controller may be used. A servo controller may be separate from, or integrated with, robotic assembly 102. In some embodiments, the servo controller and robotic assembly are provided as part of a robotic arm cart positioned adjacent to the patient's body.

The control system 112 may further include a virtual visualization system to provide navigation assistance to the interventional instruments 104. Virtual navigation using the virtual visualization system is based upon reference to an acquired dataset associated with the three dimensional structure of the anatomical passageways. More specifically, the virtual visualization system processes images of the surgical site recorded and/or modeled using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional model of a partial or an entire anatomical organ or anatomical region. The model describes the various locations and shapes of the passageways and their connectivity. The images used to generate the model may be recorded preoperatively or intra-operatively during a clinical procedure. In an alternative embodiment, a virtual visualization system may use standard models (i.e., not patient specific) or hybrids of a standard model and patient specific data. The model and any virtual images generated by the model may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display an interventional implement together with preoperatively recorded surgical images, such as those from a virtual visualization system, are known. For example U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety, discloses one such system.

The robotic interventional system 100 may further include optional operation and support systems (not shown) such as illumination systems, steering control systems, irrigation systems, and/or suction systems. In alternative embodiments, the robotic system may include more than one robotic assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
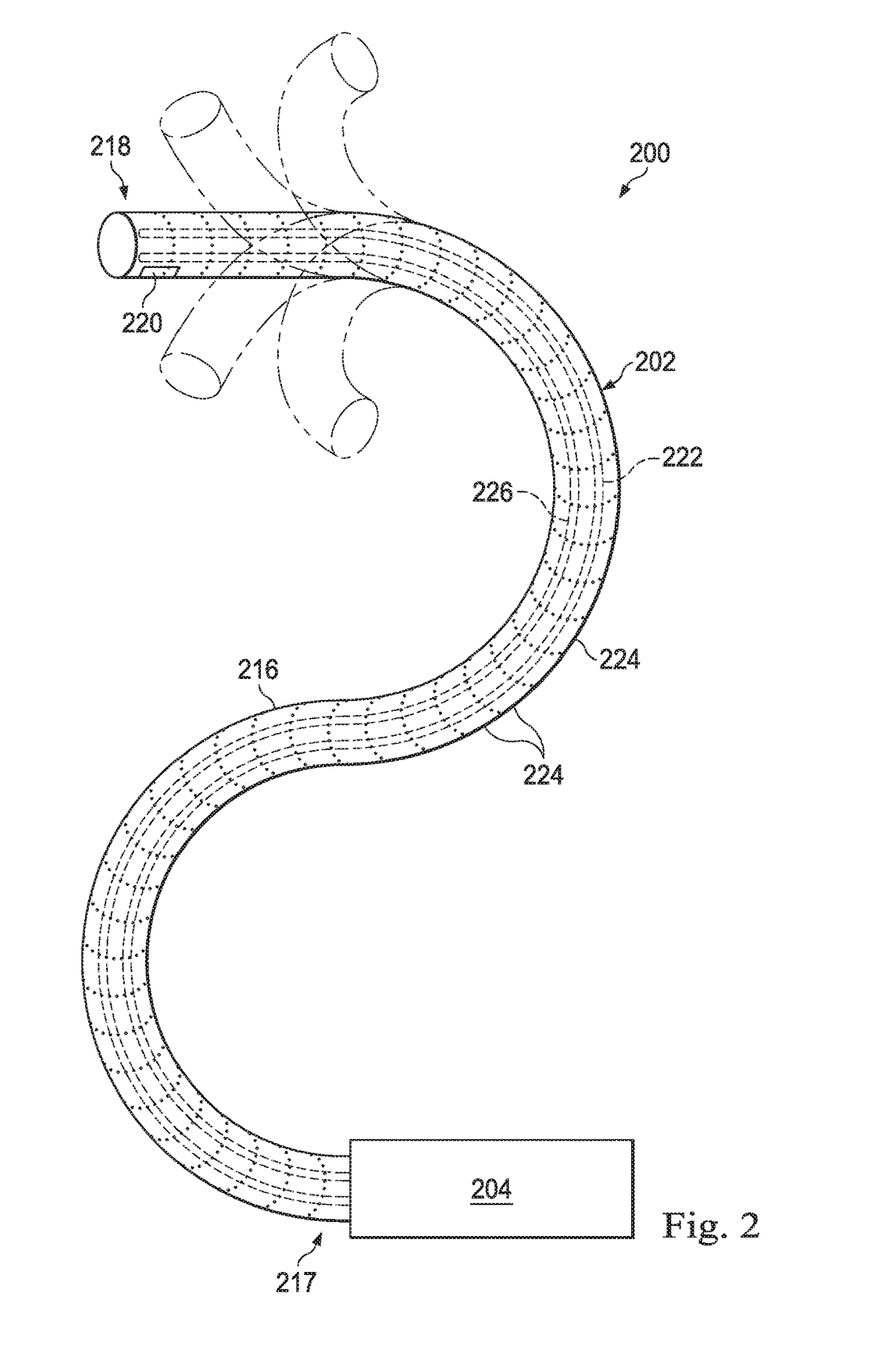
FIG. 2 illustrates an interventional instrument system utilizing aspects of the present disclosure.

FIG. 2 illustrates an interventional instrument system 200 which may be used as the interventional instrument system 104 of robotic interventional system 100. Alternatively, the interventional instrument system 200 may be used for non-robotic exploratory procedures or in procedures involving traditional manually operated interventional instruments, such as endoscopy.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, pose, and/or shape of the catheter tip at distal end 218 and/or of one or more segments 224 along the body 216. The entire length of the body 216, between the distal end 218 and the proximal end 217 may be effectively divided into the segments 224. If the instrument system 200 is an interventional instrument system 104 of a robotic interventional system 100, the shape sensor 222 may be a component of the sensor system 108. If the instrument system 200 is manually operated or otherwise used for non-robotic procedures, the shape sensor 222 may be coupled to a tracking system that interrogates the shape sensor and processes the received shape data.

The shape sensor system 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the catheter may be determined using other techniques. For example, if the history of the catheter's distal tip pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber may include multiple cores within a single cladding. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

As described, the optical fiber may be used to monitor the shape of at least a portion of the catheter system 202. More specifically, light passing through the optical fiber is processed to detect the shape of the catheter system 202 and for utilizing that information to assist in surgical procedures. The sensor system (e.g. sensor system 108) may include an interrogation system for generating and detecting the light used for determining the shape of the catheter system 202. This information, in turn, can be used to determine other related variables, such as velocity and acceleration of the parts of an interventional instrument. The sensing may be limited only to the degrees of freedom that are actuated by the robotic system, or may be applied to both passive (e.g., unactuated bending of the rigid members between joints) and active (e.g., actuated movement of the instrument) degrees of freedom.

The interventional instrument system may optionally include a position sensor system 220. The position sensor system 220 may be an electromagnetic (EM) sensor system that includes one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The flexible catheter body 216 includes a channel sized and shaped to receive an auxiliary tool 226. Auxiliary tools may include, for example, image capture probes, biopsy devices, laser ablation fibers, or other surgical, diagnostic, or therapeutic tools. Auxiliary tools may include end effectors having a single working member such as a scalpel, a blade, an optical fiber, or an electrode. Other end effectors may include a pair or plurality of working members such as forceps, graspers, scissors, or clip appliers, for example. Examples of electrically activated end effectors include electrosurgical electrodes, transducers, sensors, and the like. In various embodiments, the auxiliary tool 226 may be an image capture probe including a distal portion with a stereoscopic or monoscopic camera disposed near the distal end 218 of the flexible catheter body 216 for capturing images (including video images) that are processed for display. The image capture probe may include a cable coupled to the camera for transmitting the captured image data. Alternatively, the image capture instrument may be a fiber-optic bundle, such as a fiberscope, that couples to the imaging system. The image capture instrument may be single or multi-spectral, for example capturing image data in the visible spectrum, or capturing image data in the visible and infrared or ultraviolet spectrums.

The flexible catheter body 216 may also house cables, linkages, or other steering controls (not shown) that extend between the instrument body 204 and the distal end 218 to controllably bend or turn the distal end 218 as shown for example by the dotted line versions of the distal end. In embodiments in which the instrument system 200 is actuated by a robotic assembly, the instrument body 204 may include drive inputs that couple to motorized drive elements of the robotic assembly. In embodiments in which the instrument system 200 is manually operated, the instrument body 204 may include gripping features, manual actuators, and other components for manually controlling the motion of the instrument system. The catheter system may be steerable or, alternatively, may be non-steerable with no integrated mechanism for operator control of the instrument bending. Also or alternatively, the flexible body 216 can define one or more lumens through which interventional instruments can be deployed and used at a target surgical location.

In various embodiments, the interventional instrument system 200 may include a flexible bronchial instrument, such as a bronchoscope or bronchial catheter for use in examination, diagnosis, biopsy, or treatment of a lung. The system is also suited for navigation and treatment of other tissues, via natural or surgically created connected passageways, in any of a variety of anatomical systems including the colon, the intestines, the kidneys, the brain, the heart, the circulatory system, or the like.

When using an interventional instrument system 200 to conduct a procedure within a patient it may be desirable for the surgeon to have simultaneous access to various forms of data related to the procedure, as described herein. For instance, when guiding an interventional instrument through certain portions of the anatomy such as the respiratory system, an endoscope may be too large to fit safely through the anatomy alongside the interventional instrument system 200. In such procedures, the surgeon may wish to supplement or replace the display of an endoscopic camera with the display of preoperative or intraoperative images of the type described above. Additionally, the surgeon may wish to supplement the display of an endoscopic camera with the display of an overview representation of the anatomy indicating the location of the interventional instrument relative to the procedure site or a particular target location within the anatomy.

Figure 3:
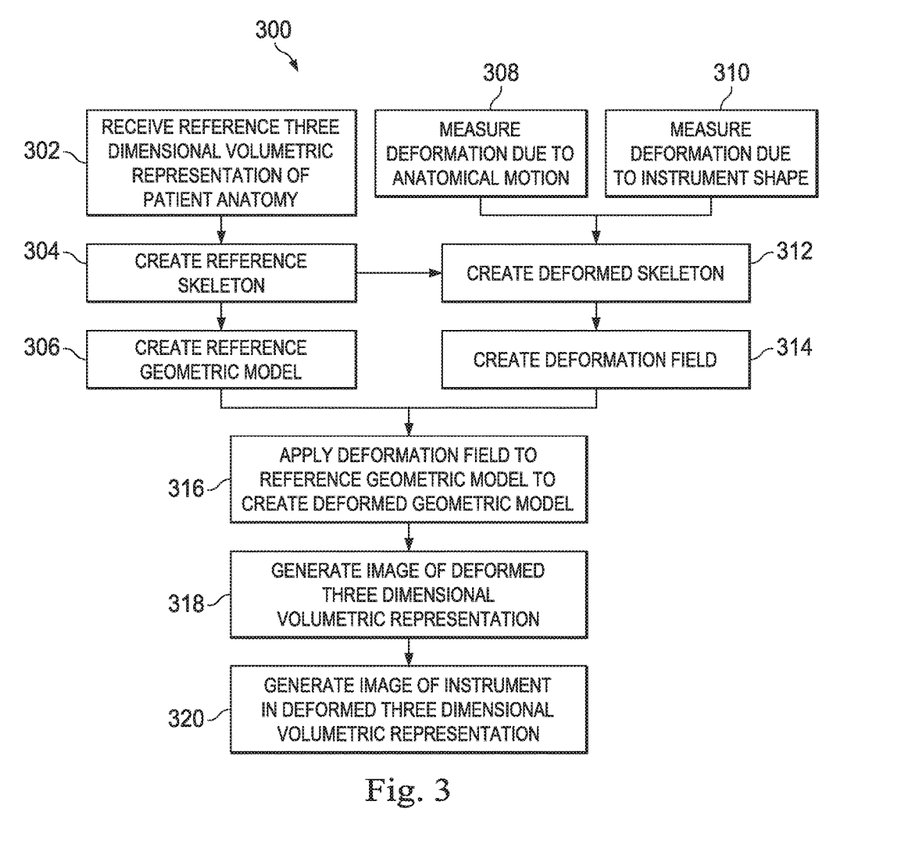
FIG. 3 illustrates a method for generating a dynamic display of a model of anatomic passageways in a deformed state.
Figure 4:
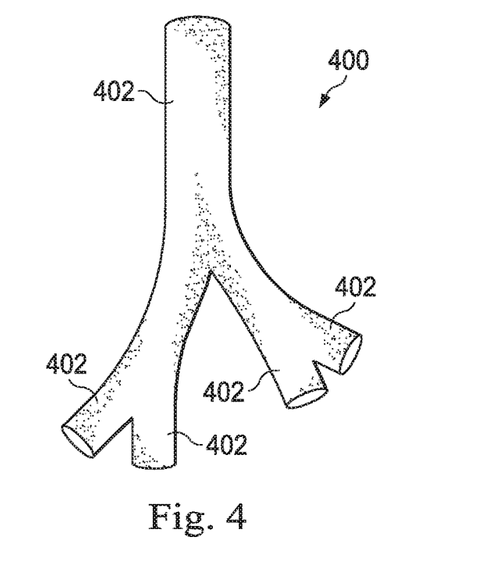
FIG. 4 illustrates a three dimensional volumetric representation of anatomic passageways in a reference state.

FIG. 3 illustrates a method 300 for generating a dynamic display of a three dimensional volumetric representation of anatomic passageways in a deformed state. At 302, a three dimensional volumetric representation (i.e., a solid model) of anatomic passageways of a patient anatomy is received or created from preoperatively or intra-operatively generated images using technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. FIG. 4 illustrates at least a portion of a three dimensional volumetric representation 400 of patient anatomic passageways as received or created at step 302 of the method 300. The three dimensional volumetric representation 400 represents the various lung passageways 402 in a reference state, such as a full exhalation state of a patient's breathing cycle.

Figure 5:
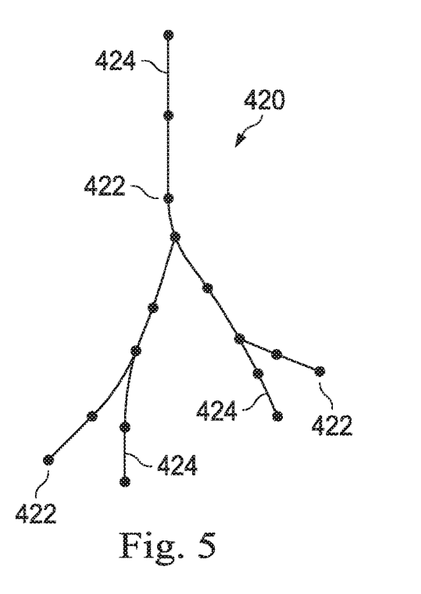
FIG. 5 illustrates a skeletal tree based on the reference model of FIG. 4.

Referring again to FIG. 3, the method 300 further includes, at 304, creating a piece-wise rigid reference skeleton tree of nodes and linkages from the reference model in the reference state. FIG. 5 illustrates a skeleton tree 420 based on the three dimensional volumetric representation 400 and includes a plurality of nodes 422 interconnected by linkages 424 to approximate the structure of the three dimensional volumetric representation 400. The nodes 402 of the skeleton tree 420 may be located at bifurcations of the anatomic passageways, at points of significant bend or twist, and/or at any other point along the anatomic passageway. The nodes may be generally centered within the anatomic passageways, but in alternative embodiments may be located along passageway walls or at other locations with respect to reference structures of the anatomy. The linkages 424 are straight segments that extend between the nodes. The linkages are generally centered within the anatomic passageways, but in alternative embodiments may be located along passageway walls or at other locations with respect to reference structures of the anatomy.

Figure 6:
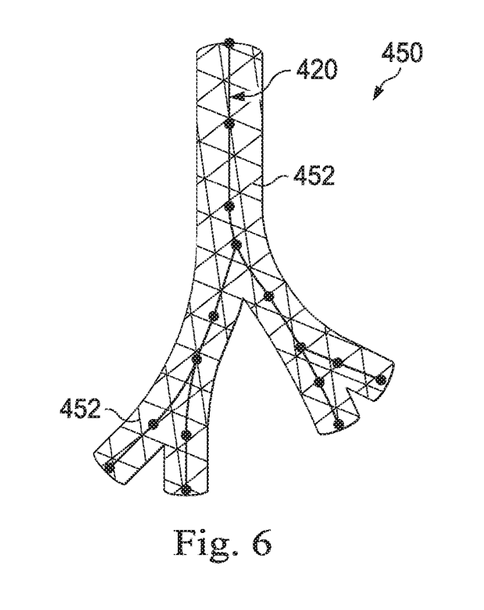
FIG. 6 illustrates a geometric model based on the reference model of FIG. 4.

Referring again to FIG. 3, the method 300 further includes, at 306, creating a reference geometric model. In one embodiment, as shown in FIG. 6, the geometric model 450 is a polygon mesh model comprised of a plurality of triangles 452 representing the a surface (interior or exterior) of the anatomic passageways. For example, a mesh model for a portion of an anatomic passageway may include approximately 130,000 triangles. In alternative embodiments, the polygon mesh model may comprise quadrilaterals or other flat, convex, or concave polygons. Each vertex of mesh model 450 may be bound to one of the nodes 422 the skeleton tree 420. Thus, each vertex of the mesh model 450 bound to a selected node 422 is also bound to the skeleton linkages 424 connected to that selected node.

Referring again to FIG. 3, the method 300 further includes, at 308, measuring at least one deformation of the anatomic passageways due to anatomical motion. Many regions of the patient anatomy are dynamic in normal function (e.g., heart, lungs, kidneys, liver, blood vessels). In this embodiment, the anatomical motion may be cyclical anatomical motion of the lungs caused by, for example, respiration or the cardiac cycle. The deformation is measured in at least one state of the anatomic cycle different from the state of the reference state. For example, if the reference state for the respiration cycle is full exhalation, the deformed state may be at a state of full inhalation. Additionally or alternatively, the deformed state may occur at a state between full inhalation and full exhalation. If the anatomic motion includes motion due to the cardiac cycle, the reference state may be, for example, the early diastole state and the deformed state may be another phase of the cardiac cycle such as atrial systole, isovolumic ventricular contraction, ventricular ejection, or isovolumic ventricular relaxation states. The deformation of the anatomic passageways may be determined from preoperative or intra-operative images using any of the previously described imaging technologies, from shape sensor measurements, from position sensor measurements, or other known methods of measuring deformation due to motion.

At 310, the method 300 includes measuring deformation of the anatomic passageways due to forces applied by an interventional instrument (e.g., catheter 202) positioned internal to the passageways. The shape of the interventional instrument may be sensed using any of the above described methods for instrument shape sensing, including, for example the use of an optical shape sensing fiber.

Figure 7:
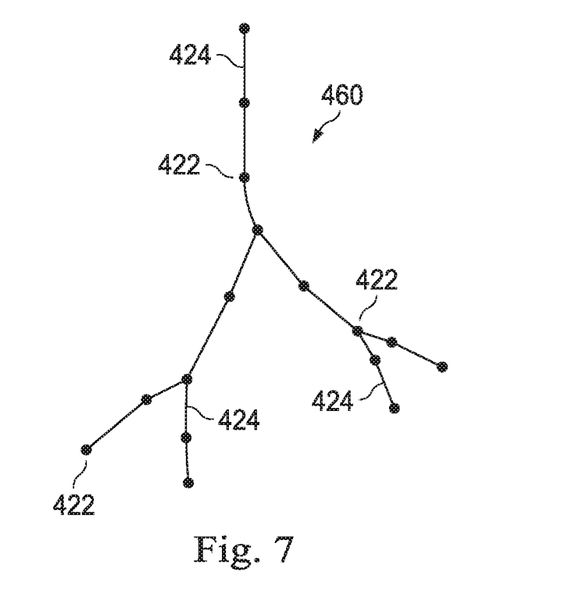
FIG. 7 illustrates the measurement of deformation of the anatomic passageways in a first state of deformation.
Figure 8:
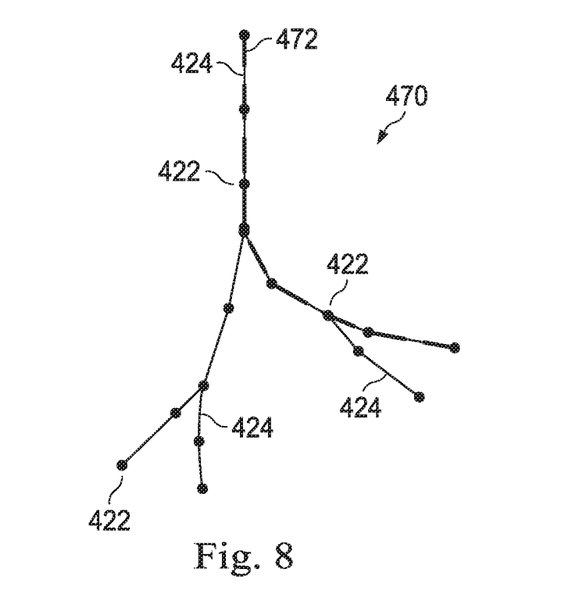
FIG. 8 illustrates the measurement of deformation of the anatomic passageways in a second state of deformation.
Figure 9:
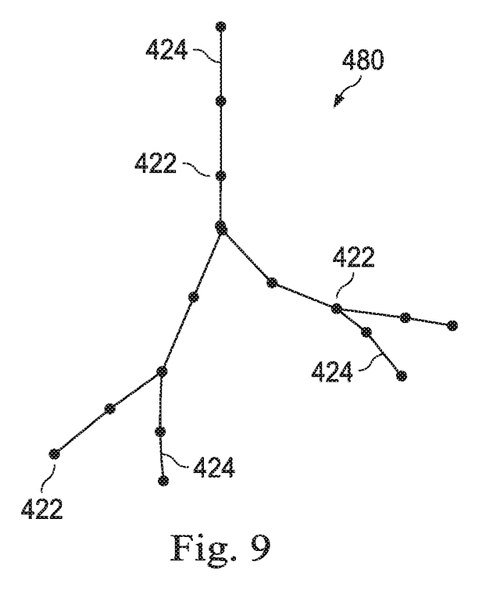
FIG. 9 illustrates a skeletal tree based on a composite deformation of the anatomic passageways.

At 312, the method 300 includes creating a skeleton tree deformed by the influence of the anatomical motion and the interventional instrument. FIG. 7 illustrates a skeleton tree 460 of the anatomic passageways in a deformed state due to anatomic motion. In this illustration, the lung passageways are in the deformed state of full inspiration. In the deformed skeleton 460, the position of the nodes 422 and the position and orientation of the linkages 424 are modified to align with the anatomic passageways from the imaged anatomy in the deformed state. FIG. 8 illustrates a skeleton tree 470 of the anatomic passageways in the reference state of expiration but in a deformed state due to forces applied by an interventional instrument 472 within some of the anatomic passageways. In the deformed skeleton 470, the position of the nodes 422 and the position and orientation of the linkages 424 are modified based on the shape measurements for the interventional instrument 472. The shape of the interventional instrument 472 may directly deform the passageways in which the interventional instrument is located but may also indirectly deform the adjacent passageways due to forces applied to the tissue connecting the passageways. FIG. 9 illustrates a skeleton tree 480 of the anatomic passageways in a deformed state due to the combination of anatomic motion (e.g., full inspiration FIG. 7) and forces applied by the interventional instrument (e.g., FIG. 8). In various alternative embodiments, deformations of the anatomical passageways caused by other forces may be measured and used to create the composite deformed skeleton tree.

Figure 10:
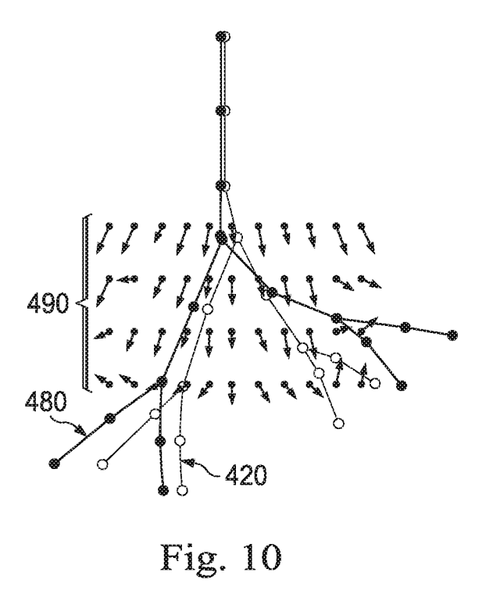
FIG. 10 illustrates a deformation field describing the deformation of the anatomic passageways.

Referring again to FIG. 3, the method 300 further includes, at 314, creating a deformation field to describe the measured deformations due to anatomical motion and/or interventional instrument forces. For example, the deformation field may include a three dimensional field vector array describing the deformation of the anatomical passageways from the full exhalation reference state to the full inhalation deformation state with a sequence of intermediate deformation states between the reference state and the full deformation state. As illustrated in FIG. 10, a deformation field 490 may include a three dimensional field vector array describing the three dimensional deformation of skeleton tree 420 into the skeleton tree 480.

Figure 11:
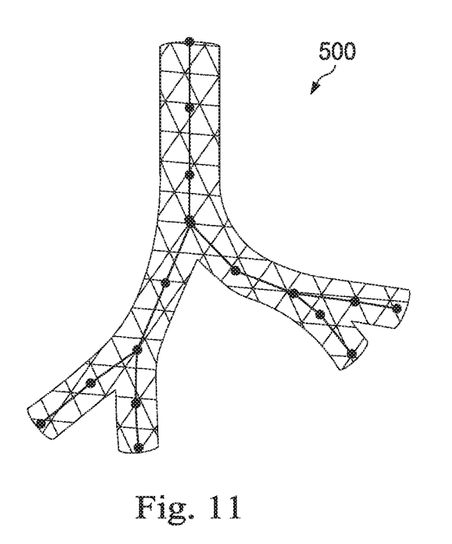
FIG. 11 illustrates a three dimensional geometric model of the anatomic passageways with the composite deformation.

Referring again to FIG. 3, the method 300 further includes, at 316, applying the deformation field to the reference geometric model to create a deformed geometric model. Generally, for each vertex in the reference mesh model 450, an interpolation of the deformation field 490 is performed at each time t. Each vertex from the reference mesh model 450 is then transformed into a corresponding vertex of a deformed mesh model 500 (FIG. 11).

Linear blend skinning (LBS) techniques, known to those of skill in the art, may be used in the creation of the deformed mesh model. With LBS techniques, each vertex of each triangle 452 of the mesh model 450 is bound to the skeleton tree 420 which is responsible for deforming the vertex. In LBS terminology, the linkages of the skeleton are considered the "bones" and provides the "bone influences." Each vertex may also be assigned a weight ($w_i$) for each linkage in the skeleton that influences the vertex. The weighting assignments are such that for each weight, $0 \leq w_i \leq 1$ and $\Sigma w_i = 1$. The weights may be found experimentally by creating different skeleton poses and then changing the weights until the mesh deforms accordingly. To deform each vertex (v) from its initial pose in the mesh model 450, a weighted combination of the vertex deformed by the skeleton linkages is used:

Deformation Formula:

$$v_{deformed} = \sum_{i=1}^{N} w_i * M_i * v_{initial}$$

where N is the number of bone influences, i is a link in the skeleton and M is an absolute link transform matrix, such as the deformation field 490, which describes the skeletal deformation.

An example method for determining the weightings is provided. With two linkage influences (i.e., bone influences) for a selected vertex v of the mesh, N=2 in the deformation formula. To determine $w_1$ and $w_2$ for the vertex v, the two closest links to v are chosen. The first closest link is $l_1$ and the second closest link is $l_2$. The distance between v and $l_1(l_2)$ is $d_v, l_1$, $(d_v, l_2)$, defined as the shortest Euclidean distance between v and a point of $l_1(l_2)$.

Figure 16:
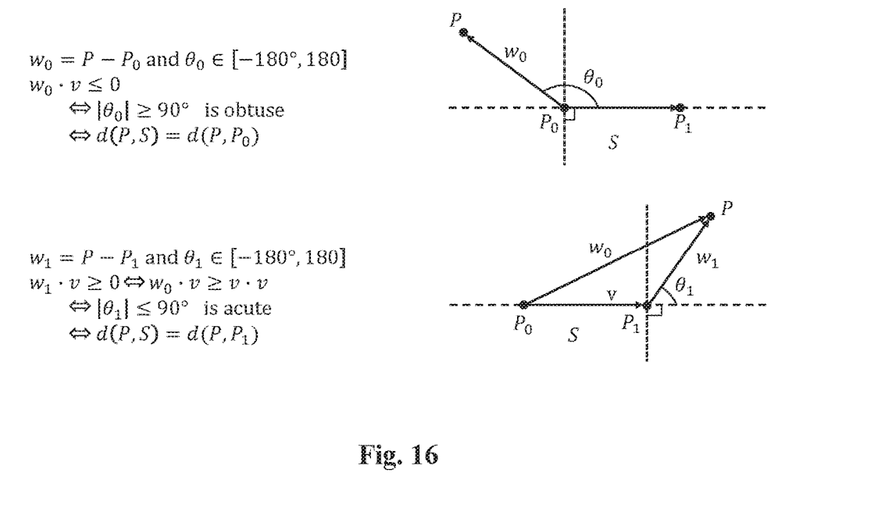
FIG. 16 illustrates an algorithmic method for determining weightings of one or more vertices of a deformed mesh model.

To compute $d_v, l_1$ and $d_v, l_2$, the dot product of vectors is applied to test whether the shortest distance between a point P (at the vertex v) and a segment S (i.e., a linkage of the skeleton) is between P and one of the endpoints of S. FIG. 16 illustrates the above-described testing.

The algorithm may also be represented as:
distance(Point P, Segment P0:P1)
{
  v=P1−P0
  w=P−P0
  if ((c1=w·v)<=0)
    return d(P, P0)
  if ((c2=v·v)<=c1)
    return d(P, P1)
  b=c1/c2
  Pb=P0+bv
  return d(P, Pb)
}

Thus, $w_1$ and $w_2$ can be computed as the normalization of $d_v, l_1$ and $d_v, l_2$:

$$w_1 = \frac{d_v, l_1}{d_v, l_1 + d_v, l_2}$$

$$w_2 = \frac{d_v, l_2}{d_v, l_1 + d_v, l_2}$$

Thus, the weightings for each vertex of the mesh can be determined and each deformed vertex ($v_{deformed}$) in the mesh may be determined. An implementation of the mesh model deformation using a graphics processing unit (GPU) is provided at FIG. 14.

Figure 12:
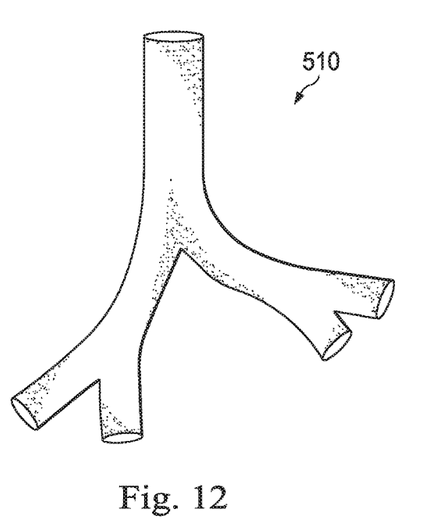
FIG. 12 illustrates the three dimensional volumetric representation of anatomic passageways of FIG. 4 rendered with the composite deformation.

Referring again to FIG. 3, the method 300 further includes, at 318, deforming the reference three dimensional volumetric representation 400 into alignment with the deformed mesh to generate an image of the deformed three dimensional volumetric representation 510 as shown in FIG. 12.

Figure 13:
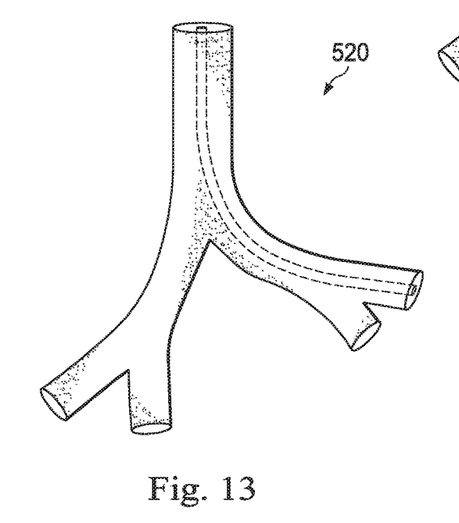
FIG. 13 illustrates the deformed three dimensional volumetric representation of anatomic passageways of FIG. 12 with the interventional instrument.

At 320, a composite image 520 (FIG. 13) is generated displaying the deformed three dimensional volumetric representation 510 or deformed mesh model 450 with an image of the interventional instrument 472.

To speed the creation of the deformed mesh model such that the deformed model may be dynamically displayed at an approximately real-time display rate, a software and/or hardware based accelerator, such as a parallel computing platform that uses GPU, may be used. With such a computing platform, the deformed images of the anatomic passageways, from the reference state to the full deformation state and including all of the intermediate deformation states may be displayed. The GPU may allow display of the reference and deformed state images at a rate of approximately 30 different frames per second and in some embodiments at a rate of approximately 50 different frames per second.

Figure 14:
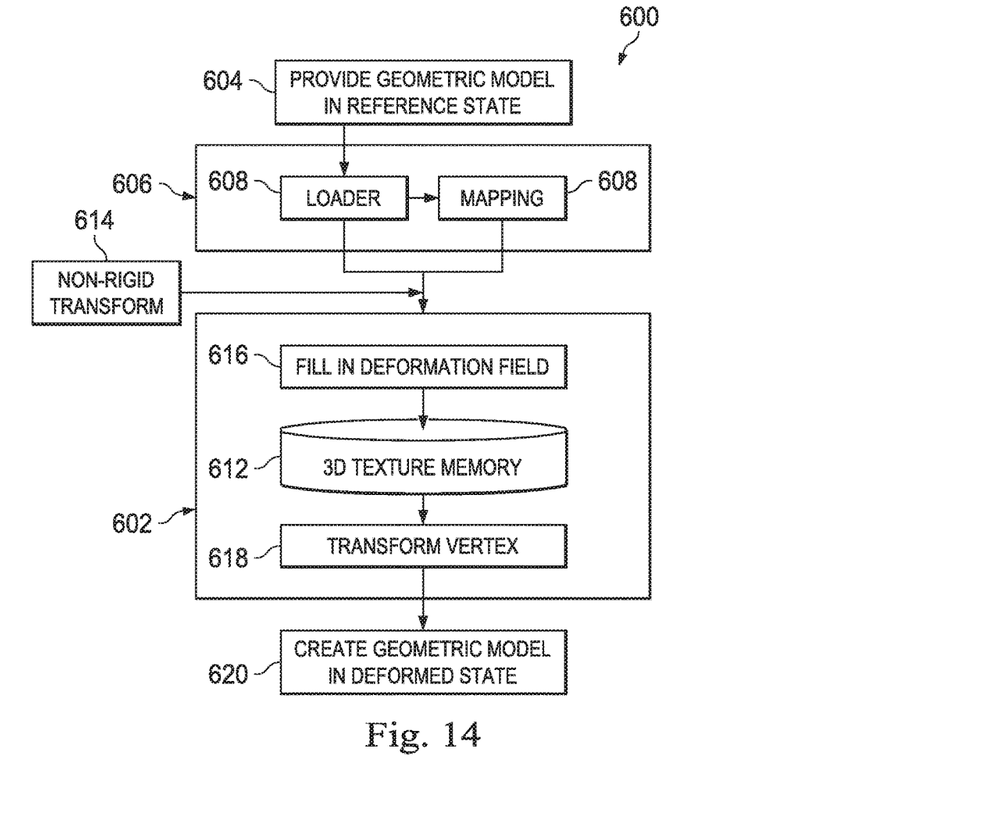
FIG. 14 illustrates a method of mesh model deformation using a graphical processing unit (GPU).

FIG. 14 illustrates a method 600 of mesh model deformation [e.g., step 316 of method 300] using a GPU 602. At 604, the mesh model in the reference state (e.g., mesh 450) is provided to a central processing unit (CPU) 606. A loader 608 running on the CPU 606 loads the mesh model to a main memory (not shown). From the memory, the mesh model is transferred to the GPU 602.

Figure 15:
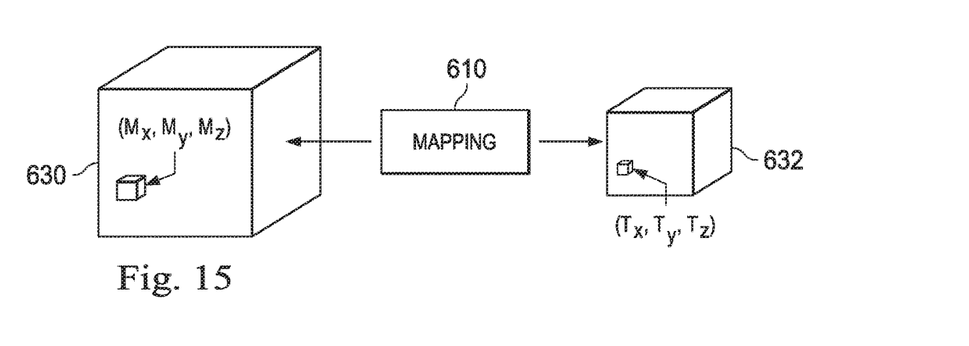
FIG. 15 illustrates a mapping technique for mapping between a mesh space and a three dimensional texture space stored in a three dimensional memory.

A mapping phase 610 is also performed on the CPU. FIG. 15 illustrates a mapping technique for mapping between the mesh space 630 (e.g., a portion of the mesh model 450) to a 3D texture space 632 that is stored in 3D texture memory 612. The 3D texture memory 612 on the GPU 602 stores a rigid transform for each node of the skeleton tree and for interpolated coordinates between the skeleton nodes. The 3D texture memory provides a fast and convenient format for storing the rigid transforms for the skeleton nodes and for interpolating transforms for coordinates in between the nodes. The speed of the interpolation allows for the transformation and movement of the mesh model bound to the skeleton model in approximately real time. The use of rigid transforms over many constituent nodes of the skeleton approximates a non-rigid transform over the entire mesh model space. Each $(T_x, T_y, T_z)$ texture space coordinate in a 3D texture memory space 632, is mapped to a corresponding mesh space coordinate $(M_x, M_y, M_z)$ in the mesh model space 630. For $(M_x, M_y, M_z)$, closest links $l_1(l_2)$ and weightings $w_1(w_2)$ are determined as described above for the LBS technique. If $(M_x, M_y, M_z)$ is too far from any link of the skeleton, than $w_1=w_2=0$. To save the memory space, the output of the mapping phase 610 is a mapping table (shown below) with 5 columns if and only if $w_1 \neq 0$.

| $(T_x, T_y, T_z)$ | Index of $l_1$ | $w_1$ | Index of $l_2$ | $w_2$ |
| --- | --- | --- | --- | --- |

The mapping table may only need to be computed once for each deformation. The mapping table is moved to the GPU 602.

For each time t, a non-rigid transform 614 is moved to the GPU 602. The non-rigid transform algorithm 614 is used to compute a rigid transform for each node of the skeleton tree 420 to describe how that node should move based on the deformed skeleton tree 480. At 616, the non-rigid transform 614 is used by the GPU 602 to compute a transform for each node in the skeleton tree. Based on the created mapping table, a full deformation field is developed, from the transformed skeleton tree nodes, for each interpolated coordinate in the 3D texture space 632. The 3D texture memory 612 stores the transforms for each coordinate in the 3D texture space 632. The fields of the 3D texture memory 612 are filled simultaneously by the GPU. Separate threads (i.e., small sequences of independently managed programmed instructions) of the GPU work to compute a deformation value, using the Deformation Formula provided above, for each coordinate of the 3D texture memory. The 3D texture memory in the GPU serves two purposes. First, the dimensions of the texture are much smaller than the model space. For example, the 3D texture memory may use a 128×128×128 voxel array and the model space may use a 1024×1024×1024 voxel array. Second, fetching the value in the 3D texture memory of the GPU with linear interpolation is very fast.

At 618, with one thread working on each vertex of the mesh model 450, a thread fetches a value (using the mapping table) from the 3D texture memory 612 that corresponds to the position of the vertex in the initial mesh model 450 and transforms it into a deformed vertex. At 620, with a deformed vertex created for each of the reference state vertices, a deformed mesh model is generated and displayed. The display of the deformed mesh model may be presented dynamically with the display of the deforming mesh model updated at a high display rate corresponding to the near real-time deformation of the patient anatomy. For example, the rate of display may be approximately 30 or more frames per second. Thus, a clinician navigating an interventional instrument through the patient anatomy is provided with a current image of the patient anatomy in its current state of deformation.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A processing system comprising:
    a processor; and
    a memory having computer readable instructions stored thereon, the computer readable instructions, when executed by the processor, cause the system to:
        receive a reference three dimensional volumetric representation of a branched anatomical formation in a reference state;
        obtain a reference tree of nodes and linkages based on the reference three dimensional volumetric representation;
        obtain a reference three dimensional geometric model based on the reference tree;
        detect deformation of the branched anatomical formation due to anatomical motion based on measurements from a shape sensor;
        obtain a deformed tree of nodes and linkages based on the detected deformation;
        create a three dimensional deformation field that represents the detected deformation of the branched anatomical formation; and
        apply the three dimensional deformation field to the reference three dimensional geometric model to create a deformed three dimensional geometric model of the branched anatomical formation in a deformed state.

2. The processing system of claim 1, wherein the computer readable instructions, when executed by the processor, cause the system to perform operations including:
    dynamically display an image of the deformed three dimensional geometric model of the branched anatomical formation in the deformed state.

3. The processing system of claim 2, wherein displaying the image of the deformed three dimensional geometric model of the branched anatomical formation in the deformed state includes displaying a sequence of images of intermediate deformations of the branched anatomical formation.

4. The processing system of claim 2, wherein the computer readable instructions, when executed by the processor, cause the system to perform operations including:
    display a composite image including an image of an interventional instrument positioned within the branched anatomical formation and the dynamically displayed image of the deformed three dimensional geometric model of the branched anatomical formation in the deformed state.

5. The processing system of claim 4, wherein the computer readable instructions, when executed by the processor, cause the system to perform operations including:
    display the composite image in real time.

6. The processing system of claim 1 wherein the reference three dimensional geometric model is a reference mesh model having vertices and the deformed three dimensional geometric model is a deformed mesh model having vertices, and wherein applying the three dimensional deformation field to the reference three dimensional geometric model includes interpolating the three dimensional deformation field for at least one of the vertices on the reference mesh model over time.

7. The processing system of claim 6 wherein the computer readable instructions, when executed by the processor, cause the system to perform operations including:
    applying weights to the vertices of the reference mesh model.

8. The processing system of claim 6 wherein applying the three dimensional deformation field to the reference three dimensional geometric model further includes transforming at least one of the vertices from the reference mesh model to a corresponding vertex on the deformed mesh model of the branched anatomical formation in the deformed state.

9. The processing system of claim 8, wherein transforming the at least one of the vertices on the reference mesh model to the corresponding vertex on the deformed three dimensional model further includes assigning a weight to the at least one of the vertices on the reference mesh model for each linkage in a plurality of linkages that influences the at least one of the vertices on the reference mesh model.

10. The processing system of claim 1, including a graphical processing unit to apply the three dimensional deformation field to the reference three dimensional geometric model.

11. The processing system of claim 1, wherein the detected deformation is indicative of at least a periodic anatomical motion.

12. The processing system of claim 1 wherein the detected deformation is indicative of a force applied by an interventional instrument positioned within the branched anatomical formation.

13. The processing system of claim 1 wherein the detected deformation is indicative of a periodic anatomical motion and a force applied by an interventional instrument positioned within the branched anatomical formation.

14. A method comprising:
    receiving a reference three dimensional volumetric representation of a branched anatomical formation in a reference state;
    creating a reference tree of nodes and linkages based on the reference three dimensional volumetric representation;
    creating a reference three dimensional geometric model based on the reference tree;
    detecting deformation of the branched anatomical formation due to anatomical motion based on measurements from a shape sensor;
    creating a deformed tree of nodes and linkages based on the detected deformation;
    creating a three dimensional deformation field that represents the detected deformation of the branched anatomical formation from the reference state to a deformed state; and
    applying the three dimensional deformation field to the reference three dimensional geometric model to create a deformed three dimensional geometric model of the branched anatomical formation in the deformed state.

15. The method of claim 14, including:
    dynamically displaying an image of the deformed three dimensional geometric model of the branched anatomical formation in the deformed state.

16. The method of claim 15, wherein displaying the image of the deformed three dimensional geometric model of the branched anatomical formation in the deformed state includes displaying a sequence of images of intermediate deformations of the branched anatomical formation.

17. The method of claim 16, including:
    displaying a composite image including an image of an interventional instrument positioned within the branched anatomical formation and the dynamically displayed image of the deformed three dimensional geometric model of the branched anatomical formation in the deformed state.

18. The method of claim 14, wherein the reference three dimensional geometric model is a reference mesh model having vertices and the deformed three dimensional geometric model is a deformed mesh model having vertices, and wherein applying the three dimensional deformation field to the reference three dimensional geometric model includes interpolating the three dimensional deformation field for at least one of the vertices on the reference mesh model over time.

19. The method of claim 18 wherein applying the three dimensional deformation field to the reference three dimensional geometric model further includes transforming at least one of the vertices from the reference mesh model to a corresponding vertex on the deformed mesh model of the branched anatomical formation in the deformed state.

20. The method of claim 18, including:
generating an image of the reference three dimensional volumetric representation in the deformed state by deforming the reference three dimensional volumetric representation into alignment with the deformed mesh model.

\* \* \* \* \*